(12) United States Patent
Schmelz

(10) Patent No.: US 9,233,059 B2
(45) Date of Patent: Jan. 12, 2016

(54) OXIDATIVE DYEING COMPOSITION

(71) Applicant: KAO GERMANY GMBH, Darmstadt (DE)

(72) Inventor: Sandra Schmelz, Marktheidenfeld (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 14/369,361

(22) PCT Filed: Dec. 20, 2012

(86) PCT No.: PCT/EP2012/076480
§ 371 (c)(1),
(2) Date: Jun. 27, 2014

(87) PCT Pub. No.: WO2013/098209
PCT Pub. Date: Jul. 4, 2013

(65) Prior Publication Data
US 2014/0373286 A1    Dec. 25, 2014

(30) Foreign Application Priority Data
Dec. 28, 2011    (EP) ..................................... 11195937

(51) Int. Cl.
| | |
|---|---|
| *A61Q 5/08* | (2006.01) |
| *A61K 8/49* | (2006.01) |
| *A61K 8/368* | (2006.01) |
| *A61K 8/42* | (2006.01) |
| *A61Q 5/04* | (2006.01) |
| *A61Q 5/10* | (2006.01) |
| *A61K 8/22* | (2006.01) |
| *A61K 8/41* | (2006.01) |

(52) U.S. Cl.
CPC ................. *A61K 8/4926* (2013.01); *A61K 8/22* (2013.01); *A61K 8/368* (2013.01); *A61K 8/411* (2013.01); *A61K 8/42* (2013.01); *A61Q 5/04* (2013.01); *A61Q 5/08* (2013.01); *A61Q 5/10* (2013.01); *A61K 2800/52* (2013.01); *A61K 2800/88* (2013.01)

(58) Field of Classification Search
CPC ............. A61Q 5/08; A61K 8/22; A61K 8/42; A61K 8/34; A61K 2800/52
USPC ........................................................... 424/62
See application file for complete search history.

(56) References Cited

U.S. PATENT DOCUMENTS

| | | | |
|---|---|---|---|
| 7,534,272 B2 * | 5/2009 | Cassier et al. .................... 8/101 |
| 2003/0082129 A1 * | 5/2003 | Buckingham et al. ...... 424/70.12 |
| 2006/0042023 A1 * | 3/2006 | Machida ........................... 8/405 |
| 2007/0151044 A1 | 7/2007 | Cassier et al. | |
| 2008/0142033 A1 | 6/2008 | Sabbagh et al. | |
| 2011/0104090 A1 | 5/2011 | Kelton et al. | |

FOREIGN PATENT DOCUMENTS

| | | | |
|---|---|---|---|
| EP | 1 920 755 A1 | 5/2008 | |
| FR | 2 939 672 A1 | 6/2010 | |
| WO | WO 2012/089665 A2 * | 7/2012 | ............... A61K 5/08 |

OTHER PUBLICATIONS

International Search Report dated May 24, 2013, mailed Jun. 4, 2013.

* cited by examiner

*Primary Examiner* — Eisa Elhilo
(74) *Attorney, Agent, or Firm* — Norris McLaughlin & Marcus PA

(57) ABSTRACT

Present invention relates to an aqueous oxidizing composition with improved stability. The object of the present invention is an aqueous composition comprising at least one oxidizing agent, salicylic acid and/or its salts and either acetaminophen or oxyquinoline and/or its salts and having a pH between 1 and 5.

18 Claims, No Drawings

OXIDATIVE DYEING COMPOSITION

This application is a 371 application of PCT/EP2012/076480 filed Dec. 20, 2012, which claims foreign priority benefit under 35 U.S.C. §119 of European Application No. 11195937.5 filed Dec. 28, 2011, the disclosures of which are all incorporated herein by reference.

Present invention relates to an aqueous oxidizing composition with improved stability.

Oxidizing compositions are used as hair cosmetics for lightening hair colour, in hair dyeing process for achieving colours from oxidative dye precursors and coupling substances and also in permanent shaping process wherein after opening the disulfide bonds, building of the disulfide bonds is done with the aid of an aqueous oxidizing composition in order to fix the new shape.

Oxidizing agent included in such compositions does undergo a decomposition wherein oxygen is produced which leads to increase in internal pressure of the packaging material wherein such compositions are stored. This result in problems such as swelling of the packaging material and therefore the vessel may not be simply kept standing on the bench and also it may lead to a product splash when opening the lid and or closure of the vessels. These problems are aggravated especially when such compositions have relatively high viscosity as oxygen cannot easily leave the compositions and be stored at upper space in the vessel.

There is an explicit need for measures realizing higher peroxide stability in order remove the above mentioned drawbacks and at least to reduce the risks coming from peroxide instability.

There are substances known to have peroxide stabilizing effect. Use of these substances alone is also common in hair cosmetic practice. These substances are salicylic acid, acetaminophen and oxyquinoline and its salts. Use of any of these substances even at elevated concentration however has not resulted in improvement of peroxide stability and solution to the above described problems.

Inventor of the present invention has found out that use of salicylic acid in combination with either acetaminophen or oxyquinoline salt has surprisingly provided improved peroxide stability and therefore the above described problems were solved.

Therefore, the object of the present invention is an aqueous composition comprising at least one oxidizing agent, salicylic acid and/or its salts and either acetaminophen or oxyquinoline and/or its salts and having a pH between 1 and 5.

In a further preferred embodiment of the present invention, aqueous composition comprises at least one oxidizing agent, salicylic acid and/or its salts, acetaminophen and oxyquinoline and/or its salts and has a pH between 1 and 5.

Further object of the present invention is use of the composition of the present invention in treating hair.

Still another object of the present invention is a kit for treating hair comprising two or more compositions wherein one of the compositions is an aqueous composition comprising at least one oxidizing agent, salicylic acid and/or its salts and either acetaminophen or oxyquinoline and/or its salts and having a pH between 1 and 5.

Compositions of the present invention are aqueous compositions and therefore comprise at least 45% by weight water, preferably between 50 and 90%, more preferably between 55 and 85% and most preferably between 60 and 80% by weight water calculated to the total composition.

Composition of the present invention has an acidic pH, between 1 and 5, preferably between 1.5 and 4.5, more preferably between 2 and 4, and most preferably between 2.5 and 3.5. The pH of the compositions is adjusted by using commonly used organic and/or inorganic acids, preferably with inorganic acids and their salts and more preferably with phosphoric acid and its salts.

Compositions comprise at least one oxidizing agent. Suitable ones are hydrogen peroxide, urea peroxide, melamin peroxide or perborate salts. The most preferred is hydrogen peroxide. At least one oxidizing agent is comprised in the aqueous compositions at a concentration in the range of 0.1 to 25%, preferably 0.5 to 20% and more preferably 1 to 15% by weight calculated to the total composition.

Compositions comprise salicylic acid and/or it salts. Suitable salts are sodium and potassium salts. The most preferred is salicylic acid. The preferred concentration is in the range of 0.001 to 1%, more preferably 0.002 to 0.75% most preferably 0.005 to 0.5% by weight calculated to the total composition.

Compositions comprise acetaminophen at a concentration in the range of 0.001 to 1%, more preferably 0.002 to 0.75% most preferably 0.005 to 0.5% by weight calculated to the total composition.

Compositions comprise oxyquinoline and/or its salts. Suitable salts are oxyquinoline benzoate and oxyquinoline sulphate. The most preferred is oxyquinoline sulphate. Compositions comprise oxyquinoline and/or its salts at a total concentration in the range of 0.001 to 1%, more preferably 0.002 to 0.75% most preferably 0.005 to 0.5% by weight calculated to the total composition.

In a preferred embodiment of the present invention the compounds salicylic acid and/or its salts, acetaminophen and oxyquinoline and/or its salts are comprised in the compositions at a weight ratio of 1:1:0.5.

Compositions of the present invention are preferably emulsions and comprise therefore fatty alcohol, oil and surfactants as emulsifiers.

The fatty alcohols preferred are according to the following general structure

wherein $R_1$ is a linear or branched, saturated or unsaturated alkyl chain with 12 to 22 C atoms. Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 1 to 20%, more preferably 1.5 to 15% and most preferably 1.5 to 10% by weight calculated to total composition.

Compositions comprise preferably oil, more preferably natural oil and most preferably natural triglycerides. Concentration of oil varies between 0.1 and 25%, preferably 0.5 and 25% and more preferably 1 and 20%, most preferably 2 and 20%, in particular 2.5 and 15% by weight calculated to the total composition.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheat germ oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Further suitable oil components are natural oils such as paraffin oil.

Further suitable ones are synthetic oils such as silicones known with CTFA adopted name dimethicone, cyclomethicone, and arylates silicones such as phenyl trimethicone which are available commercially from Dow Corning.

Further suitable synthetic oils are fatty acid fatty alcohol esters such as octyl palmitate, isocetyl palmitate, isopropyl palmitate and octyl stearate.

Compositions preferably comprise at least one surfactant as an emulsifier. Suitable surfactants are non-ionic, cationic and anionic ones. Most preferred are non-ionic and cationic surfactants.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants. Preferred are alkyl sulphates or alkyl ether sulphates and the most preferred are alkyl ether sulphates.

Further surfactants in the compositions according to the invention are nonionic surfactants. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates. Further nonionic surfactants preferred in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20. The most preferred is ceteth, steareth and ceteareth with 20 to 35 ethoxy groups and ceteareth-30 is particularly preferred.

Compositions preferably comprise a cationic surfactant and especially a monoalkyl cationic surfactant according to the general structure

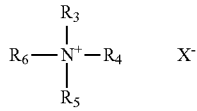

where $R_3$ is a saturated or unsaturated, branched or linear alkyl chain with 8-22 C atoms or $R_7CONH(CH_2)_n$ where $R_7$ is saturated or unsaturated, branched or linear alkyl chain with 7-21 C atoms and n has typical value of 1-4 or $R_8COO(CH_2)_n$ where $R_8$ is saturated or unsaturated, branched or linear alkyl chain with 7-21 C atoms and n has typical value of 1-4, and $R_4$, $R_5$ and $R_6$ are H or lower alkyl chain with 1 to 4 Carbon atoms, and X is typically chloride, bromide, methosulfate.

Typical examples of those ingredients are cetyl trimethyl ammonium chloride, stear trimonium chloride, palmitoyl trimonium chloride, stearyl trimonium chloride, stearamidopropyl trimonuim chloride and oleoylethyl trimethyl ammonium methosulfate. The most preferred are cetyl trimethyl ammonium chloride, stear trimonium chloride and palmitoyl trimonium chloride. Cetyl trimethyl ammonium is particularly preferred.

Compositions preferably comprise at least one polyol. With the term polyol compounds comprising two or more OH groups in their molecule are meant. Suitable nonlimited examples are propylene glycol, butyleneglycol, panthenol, and glycerine. Te most preferred is glycerine. Concentration of at least one polyol is in the range of 0.1 to 20%, preferably 1 to 15% and more preferably 1 to 10% by weight calculated to the total composition.

Compositions preferably comprise additionally at least one chelating agent. In principal any chelating agent known in the field of cosmetics is suitable for the compositions of the present invention. Preferred are ethylene diamine tetraacetic acid (EDTA) etidronic acid, galactaric acid, gluconic acid and their respective salts. Most preferred are diamine tetraacetic acid (EDTA) etidronic acid and gluconic acid and their respective salts and also their mixtures.

Total concentration of chelating agents in the compositions of the present invention is in the range of 0.01 to 2.5%, preferably 0.02 to 2%, more preferably 0.05 to 1.5% and most preferably 0.1 to 1% by weight calculated to the total composition.

Compositions may also comprise thickening agents such as polymers of any nature which may have thickening effect at the pH of the compositions which is mentioned above. With the term thickening agent it is meant that the compound has a thickening effect in the compositions as disclosed above. Non-limited examples are cellulose derivatives such as hydroxyethylcellulose, hydroxymethylcellulose, polyquesternium-10, xanthan gum and their derivatives.

Compositions of the present invention may have any consistency. Since the problems related to instability is aggravated in compositions having higher consistency, preferably the compositions of the present invention has a viscosity above or equal to 2000 mPa·s, more preferably 5000 to 25000 mPa·s and most preferably 7500 to 25000 mPa·s and in particular 10000 to 18000 mPa·s measured at 20° C. with a rotation viscoismeter.

Compositions may further comprise substances found customarily in such compositions which are not disclosed above.

The following examples are used to illustrate the invention but not to limit it.

EXAMPLE 1

| | % by weight | | | | | |
|---|---|---|---|---|---|---|
| | A | B | C | D | E | F |
| Hydrogen peroxide | 12.0 | 12.0 | 12.0 | 12.0 | 12.0 | 12.0 |
| Propylene glycol | 5.0 | 5.0 | 5.0 | 5.0 | 5.0 | 5.0 |
| Parafin oil | 5.0 | 5.0 | 5.0 | 5.0 | 5.0 | 5.0 |
| Cetearyl alcohol | 5.0 | 5.0 | 5.0 | 5.0 | 5.0 | 5.0 |
| Ceteareth-30 | 2.5 | 2.5 | 2.5 | 2.5 | 2.5 | 2.5 |
| Cetrimonium chloride | 1.0 | 1.0 | 1.0 | 1.0 | 1.0 | 1.0 |
| Phosphoric acid | | | q.s. to pH 2.0 | | | |
| EDTA | 0.1 | 0.1 | 0.1 | 0.1 | 0.1 | 0.1 |
| Salicylic acid | 0.06 | — | — | 0.03 | 0.03 | 0.02 |
| Acetaminophen | — | 0.06 | — | — | 0.03 | 0.02 |
| Oxyquinoline sulphate | — | — | 0.06 | 0.03 | — | 0.02 |
| Water | | | q.s. to pH 2.0 | | | |

All of the above compositions are emulsions and were prepared by conventional method. Viscosity of the compositions was approximately 22000 mPa·s measured at 20° C. with a Brookfield rotation viscosimeter using Spindle 5 at 5 rpm.

The above compositions were filled into PET bottles and stored at 40° C. and 50° C. for several months. After each month, stability was assessed visually by observing the bottle shape. Swelling of the bottle was assessed as:

1 No swelling at all, bottle kept its original shape
2 Slight shape change at the bottom of the bottle but bottle still stands on the table
3 Shape change at the bottom of the bottle but bottle still stands on the table
4 Clear shape change at the bottom of the bottle but bottle cannot stands on the table
5 Bottom of the bottle is almost rounded up and in no was bottle may stand on the table Results of the stability test are given in the following Table.

| | Composition | | | | | |
|---|---|---|---|---|---|---|
| | A | | B | | C | |
| Storage period | 40° C. | 50° C. | 40° C. | 50° C. | 40° C. | 50° C. |
| Start | 1 | 1 | 1 | 1 | 1 | 1 |
| 1 month | 1 | 2 | 1 | 2 | 1 | 2 |
| 2 months | 2 | 4 | 2 | 4 | 2 | 4 |
| 3 months | 2-3 | 5 | 3 | 5 | 3 | 5 |

| | Composition | | | | | |
|---|---|---|---|---|---|---|
| | D | | E | | F | |
| Storage period | 40° C. | 50° C. | 40° C. | 50° C. | 40° C. | 50° C. |
| Start | 1 | 1 | 1 | 1 | 1 | 1 |
| 1 month | 1 | 1 | 1 | 1 | 1 | 1 |
| 2 months | 1 | 1 | 1 | 1 | 1 | 1 |
| 3 months | 1 | 2 | 1 | 2 | 1 | 1 |

From the above result it is clear that using salicylic acid, acetaminophen or oxyquinoline sulphate one by one is not enough for obtaining a storage stable composition. When a composition comprises salicylic acid in combination with acetaminophen or oxyquinoline sulphate, satisfactory stability is observed. However, when three of the compounds are all comprised in the same composition, no instability was observed. It is furthermore noted that for all compositions no major viscosity changes was observed.

The invention claimed is:

1. An emulsion composition comprising
    (A) an aqueous phase comprising components (a)-(c):
        (a) a bleaching agent, consisting of one or more oxidizing agents;
        (b) salicylic acid and/or a salt of salicylic acid;
        (c) a compound selected from the group consisting of acetaminophen, a salt of acetaminophen, oxyquinoline and a salt of oxyquinoline; and
    (B) an oil phase comprising components (d)-(f):
        (d) a fatty alcohol;
        (e) an oil consisting of at least one natural triglyceride selected from the group consisting of argan oil, shea butter oil, karite oil and mixtures thereof or at least one natural oil consists of paraffin oil, wherein the oil is present at a concentration between 2.5 to 15% by weight, calculated to the total composition; and
        (f) a surfactant as an emulsifier,
    wherein the composition has a pH between 1 and 5.

2. The composition according to claim 1, comprising: acetaminophen or a salt of acetaminophen; and oxyquinoline or a salt of oxyquinoline.

3. The composition according to claims 1, further comprising: at least 45% by weight water, calculated to total composition.

4. The composition according to claim 1, wherein the at least one oxidizing agent is selected from the group consisting of hydrogen peroxide, urea peroxide, melamin peroxide and perborate salts.

5. The composition according to claim 4, wherein the at least one oxidizing agent is hydrogen peroxide and is present at a concentration in the range of 0.1 to 25% by weight, calculated to the total composition.

6. The composition according to claim 1, wherein component (c) is oxyquinoline salt selected from oxyquinoline benzoate and oxyquinoline sulphate.

7. The composition according to claim 6, wherein oxyquinoline sulphate is present at a concentration in the range of 0.001 to 1% by weight, calculated to the total composition.

8. The composition according to claim 1, wherein the salicylic acid is present at a concentration in the range of 0.001 to 1% by weight, calculated to the total composition.

9. The composition according to claim 1 wherein, the acetaminophen is present at a concentration in the range of 0.001 to 1% by weight, calculated to the total composition.

10. The composition according to claim 1, comprising: non-ionic and cationic surfactants, wherein the cationic surfactant is selected from compounds according to general structure

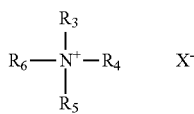

where $R_3$ is a saturated or unsaturated, branched or linear alkyl chain with 8-22 carbon atoms or $R_7CONH(CH_2)_n$ where $R_7$ is saturated or unsaturated, branched or linear alkyl chain with 7-21 carbon atoms and n has a value of 1-4 or $R_8COO(CH_2)_n$ where $R_8$ is saturated or unsaturated, branched or linear alkyl chain with 7-21 carbon atoms and n has a value of 1-4, and $R_4$, $R_5$ and $R_6$ are H or lower alkyl chain with 1 to 4 carbon atoms, and X is selected from the group consisting of chloride, bromide, methosulfate.

11. The composition according to claim 1, further comprising: at least one chelating agent.

12. The composition according to claim 1, wherein the composition has a viscosity above or equal to 2000 mPa·s measured at 20° C. with a rotation viscosimeter.

13. The composition according to claim 1, wherein the fatty alcohol comprises cetearyl alcohol.

14. The composition according to claim 1, wherein the salicylic acid or a salt of salicylic acid and the oxyquinoline or a salt of oxyquinoline are present in the composition at a weight ratio of 1:1.

15. The composition according to claim 1, wherein the oxyquinoline salt is present and selected from oxyquinoline benzoate.

16. An emulsion composition comprising an aqueous phase and an oil phase:
    said aqueous phase comprises
        a bleaching agent, consisting of one or more oxidizing agents;
        at least one compound selected from salicylic acid and a salt of salicylic acid;
        at least one compound selected from acetaminophen and a salt of acetaminophen; and
        at least one compound selected from oxyquinoline and a salt of oxyquinoline,
        wherein the at least one compound selected from salicylic acid and a salt of salicylic acid, the at least one compound selected from acetaminophen and a salt of acetaminophen, and the at least one compound selected from oxyquinoline and a salt of oxyquinoline are present in the composition at a weight ratio of 1:1:0.5 to 1:1:1, and
    said oil phase comprises:
        a fatty alcohol;
        an oil; and
        a surfactant as an emulsifier, and
    wherein the emulsion has a pH between 1 and 5.

17. The composition according to claim 16, wherein the at least one compound selected from acetaminophen and a salt of acetaminophen and the at least one compound selected from oxyquinoline and a salt of oxyquinoline are present in the composition at a weight ratio of 1:1.

18. The composition according to claim 16, wherein the at least one compound selected from salicylic acid and a salt of salicylic acid and the at least one compound selected from oxyquinoline and a salt of oxyquinoline are present in the composition at a weight ratio of 1:1.

* * * * *